US006899863B1

(12) United States Patent
Dhellin et al.

(10) Patent No.: US 6,899,863 B1
(45) Date of Patent: May 31, 2005

(54) METHOD FOR PREPARING MEMBRANE VESICLES

(75) Inventors: Olivier Dhellin, Paris (FR); Sebastian Amigorena, Paris (FR); Philippe Rameau, Massy (FR); Joël Crouzet, Sceaux (FR)

(73) Assignees: Anosys, Inc., Institute Curie; Institute National de la Sante et de la Recherche Medicale

( * ) Notice: Subject to any disclaimer, the term of this patent is extended or adjusted under 35 U.S.C. 154(b) by 0 days.

(21) Appl. No.: 09/890,319

(22) PCT Filed: Jan. 19, 2000

(86) PCT No.: PCT/FR00/00105

§ 371 (c)(1),
(2), (4) Date: Jul. 26, 2001

(87) PCT Pub. No.: WO00/44389

PCT Pub. Date: Aug. 3, 2000

(30) Foreign Application Priority Data

Jan. 27, 1999 (FR) .......................................... 99 00886

(51) Int. Cl.$^7$ ........................ A61M 36/14; A61K 39/00; A61K 35/12; A61K 35/14
(52) U.S. Cl. .................. 424/1.21; 424/277.1; 424/520; 424/529; 424/534; 435/317.1
(58) Field of Search ...................... 435/317.1; 424/1.21, 424/277.1, 520, 529, 534, 234.1

(56) References Cited

U.S. PATENT DOCUMENTS 6,165,785 A * 12/2000 Ogle et al.

FOREIGN PATENT DOCUMENTS

WO    WO 89/00846    * 2/1989

OTHER PUBLICATIONS

The Sigma Catalog, (1997, pp. 1801–1803).*
Michaelson et al, Monographs in Neural Sciences, 1980, vol. 7, pp. 19–29. (Abstract).*
Alberts et al, Molecular Biology of the Cell, (text) 1989, pp. 1077–1079.*
The Sigma Catalog, 1997, pp. 1801 and 1815.*
Vaandrager et al, Biochimica et Biophysica Acta, 1988, vol. 939, pp. 305–314.*
Denning et al, Journal of Protozoology, 1989, vol. 36, pp. 334–340.*
Dubinsky et al, American Journal of Physiology, 1986, vol. 251, pp. C713–C720.*
Langridge–Smith et al, Biochimica et Biophysica Acta, 1984, vol. 777, pp. 84–92.*
Gordon, The Origins of Modern Biochemistry, Annals of the New York Academy of Sciences, 1979, vol. 325, pp. 95–103.*
Von der Decken, European Journal of Biochemistry, 1968, vol. 4, pp. 87–94.*
Smith et al, Oxford Dictinary of Biochemistry and Molecular Biology, 1997, p. 419.*
Nishino et al, Archives of Biochemistry and Biophysics, 2000, vol. 374, pp. 293–298. (abstract).*
Tanaka et al, Journal of Biological Chemistry, 1987, vol. 262, pp. 1374–1381. (abstract).*
Seeger, Z. Krebsforsch, 1950, vol. 57, pp. 113–120. (abstract).*
Feldman et al, PNAS, 1987, vol. 84, pp. 6775–6779.*
Reuveny et al, Developments in Biological Standardization, 1980, vol. 46, pp. 137–145. (abstract).*
Abbas et al, Cellular and Molecular Immunology, (text), 1991, p. 17.*
Thiery et al, Journal of Cell Biology, 1999, vol. 147, pp. 599–610.*
Chen et al, Journal of Chromatography, 1995,vol. 666, pp. 178–182.*
Pharmacia Biotechnology, Ion Exchange Chromatography, Principles and Methods, 1991, 3rd edition, p. 34.*
Zitvogel et al, Nature Medicine, 1998, vol. 4, pp. 594–600.*
Amigorena, (Hematology and Cell Therapy, 1997, vol. 39, pp. 87–89.*

* cited by examiner

*Primary Examiner*—Karen A. Canella
(74) *Attorney, Agent, or Firm*—Orrick, Herrington & Sutcliffe LLP

(57) ABSTRACT

This invention relates to a method of preparing membrane vesicles from a biological sample, characterised in that it comprises at least one anion exchange and/or gel permeation chromatography treatment of the sample. The invention is used to prepare vesicles of varied origins and types, particularly from antigen presenting cells or tumoral cells. The invention also relates to the vesicles obtained in this way and their uses.

15 Claims, 11 Drawing Sheets

METHOD FOR PREPARING MEMBRANE VESICLES

Figure 1:
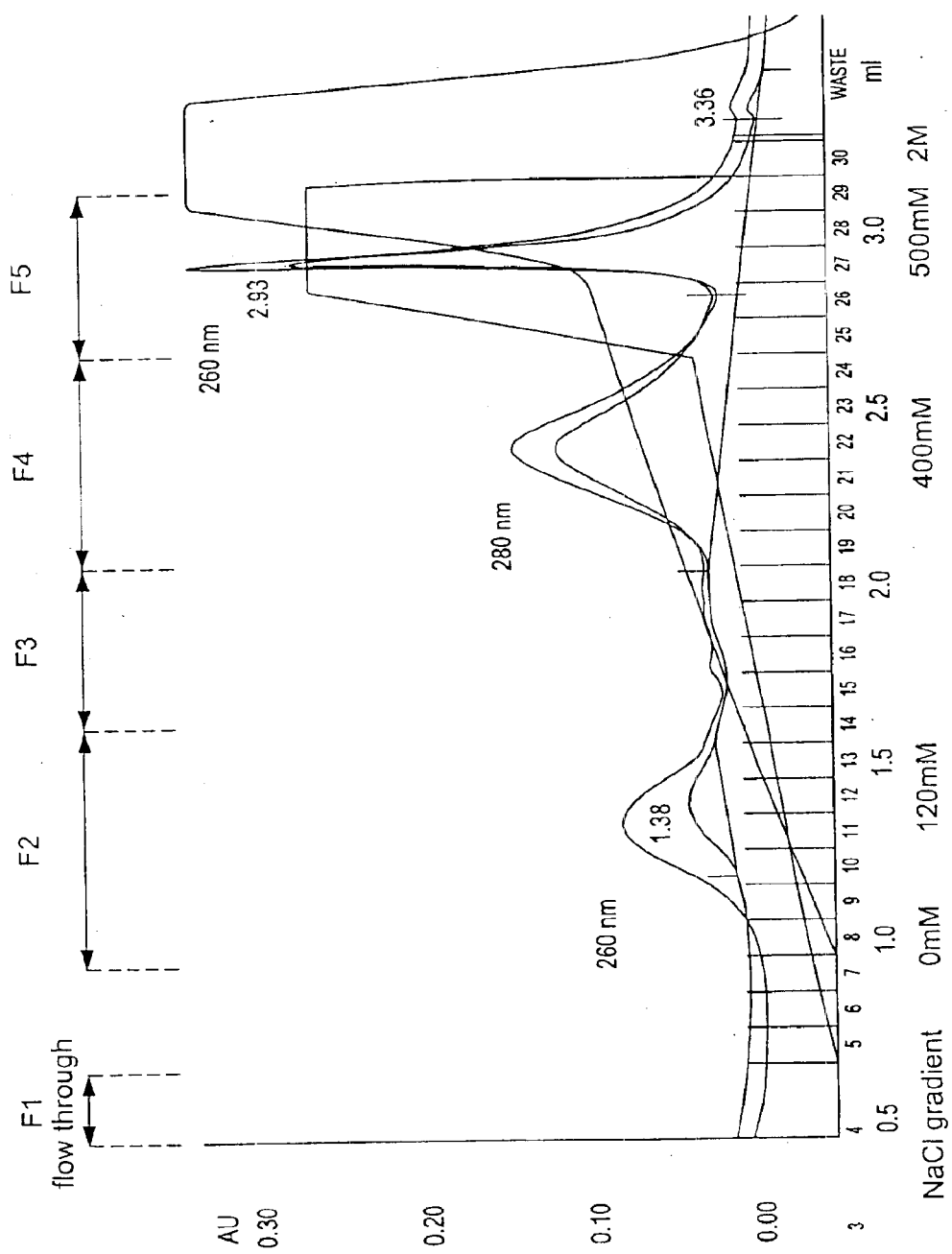

This invention relates to a new method of preparing (particularly isolating and/or purifying) membrane vesicles. The invention also relates to the membrane vesicles prepared in this way and their biological and medical uses, for example.

Membrane vesicles are vesicles, generally less than 100 nm in diameter composed of a lipid bilayer containing a cytosolic fraction. Particular membrane vesicles are more specifically obtained from intracellular compartments through fusion with the plasmic membrane of a cell, resulting in their release in biological fluids or in the supernatant of cells in culture. Such vesicles are generally referred to as exosomes. Exosomes are generally between about 50 and 90 nm in diameter, more specifically between about 60 and 80 nm and, advantageously, carry membrane proteins (particularly major histocompatibility complex proteins) which are in the same orientation as in the plasmic membrane of their original cells. In addition, depending on their origin, exosomes comprise membrane proteins such as CD40, CD80 and HSP70 and have no endoplasmic reticulum or Golgi apparatus.

Exosome release has been demonstrated from different cell types in varied physiological contexts. In this way, it has been demonstrated that B lymphocytes release exosomes carrying class II major histocompatibility complex molecules, which play a role in antigenic presentation (Raposo et al., J. Exp. Med. 183 (1996) 1161). Similarly, it has been demonstrated that dendritic cells produce exosomes (also referred to as dexosomes), with specific structural and functional characteristics and playing a role in immune response mediation, particularly in cytotoxic T lymphocyte stimulation (Zitvogel et al., Nature Medicine 4 (1998) 594). It has also been demonstrated that tumoral cells secrete specific exosomes (also referred to as texosomes) in a regulated manner, carrying tumoral antigens and capable of presenting these antigens or transmitting them to antigen presenting cells (patent application No. WO99/03499). It is also known that mastocyte cells accumulate molecules in intracellular vesicular compartments, which may be secreted under the effect of signals (Smith and Weis, Immunology Today 17 (1996) 60). Therefore, as a general rule, cells appear to emit signals and communicate with each other via membrane vesicles that they release, which may carry antigenic patterns, MHC molecules or any other signal (cytokine, growth factor, etc.) with specific structural and functional characteristics, produced in different physiological situations. Therefore, these vesicles, particularly exosomes, represent a product of particular interest for diagnostic, vaccination or therapeutic applications or to deliver molecules of interest. Therefore, it would be of particular interest to have an effective method which could be used at an industrial scale to prepare membrane vesicles compatible with biological use, particularly pharmacological use.

Conventional methods to prepare membrane vesicles e.g. exosomes) involve a series of differential centrifugation steps to separate the vesicles from cells or cell debris present in the culture medium. In this way, the documents mentioned above essentially describe the preparation of vesicles with a series of centrifugations at 300 g, 10,000 g and 70,000 g or 100,000 g, the pellet obtained being taken up with a saline solution to constitute a concentrated exosome solution. This preparation may be analysed using conventional biochemical techniques used to evaluate the protein composition of the exosomes. A preferred biochemical technique consists of electrophoresis in a denaturing medium combined with staining of the total proteins or the detection of specific proteins using antibodies according to the Western Blot technique. The exosomes in the final preparation may be detected directly by electron microscopy after fixing the preparation with a 4% glutaraldehyde solution.

According to this process, the purity levels of the exosomes are satisfactory, since such preparations have made it possible to demonstrate the biological activity and the anti-tumoral properties in animal models. However, these prior art centrifugation processes do not enable the fine separation of membrane vesicles (e.g. exosomes) from cell proteins or certain macromolecular components (DNA, RNA) or macromolecular complexes. Therefore, these processes do not exclude the presence of unidentified contaminating biological agents, incompatible with therapeutic use in humans. In addition, these steps are difficult to extrapolate at an industrial scale, particularly when significant volumes are to be treated, or for autologous (i.e. patient by patient) ex vivo applications, in which the process must generally be applied in a confined system.

The present invention now provides a solution to this problem. The invention describes new processes for the preparation (i.e. isolation and/or purification) of membrane vesicles under conditions compatible with an industrial use and pharmacological applications. In particular, the processes according to the invention may be applied both for individualised autologous exosome preparations and for exosome preparations obtained from established cell lines, for experimental or biological use or prophylactic or therapeutic vaccination purposes, for example.

This invention is more specifically based on the use of chromatography separation methods for preparing membrane vesicles, particularly to separate the membrane vesicles from potential biological contaminants.

More specifically, a first object of this invention resides in a method of preparing membrane vesicles from a biological sample, characterised in that it comprises at least an anion exchange chromatography treatment step of the sample.

Indeed, the applicant has now demonstrated that membrane vesicles, particularly exosomes, could be purified by anion exchange chromatography. In this way, unexpectedly, it is demonstrated in this application that exosomes are resolved in a homogeneous peak after anion exchange chromatography. This result is completely unexpected given that exosomes are complex supramolecular objects composed, among other things, of a membrane, surrounding an internal volume comprising soluble proteins. In addition, exosomes contain membrane proteins.

Therefore, a preferred object of this invention relates to a method of preparing, particularly of purifying, vesicle membranes, from a biological sample, comprising at least one anion exchange chromatography step.

To apply the invention, a strong or weak, preferably strong, anion exchange may be performed. In addition, in a specific embodiment, the chromatography is performed under pressure. Thus, more specifically, it may consist of high performance liquid chromatography (HPLC).

Different types of supports may be used to perform the anion exchange chromatography. More preferably, these may include cellulose, poly(styrene-divinylbenzene), agarose, dextran, acrylamide, silica, ethylene glycol-methacrylate co-polymer, or mixtures thereof, e.g., agarose-dextran mixtures. To illustrate this, it is possible to mention the different chromatography equipment composed of supports as mentioned above, particularly the following gels: SOURCE. POROS®. SEPHAROSE®, SEPHADEX®, TRISACRYL®, TSK-GEL SW OR PW®, SUPERDEX®TOYOPEARL HW and SEPHACRYL®, for example, which are suitable for the application of this invention.

Therefore, in a specific embodiment, this invention relates to a method of preparing membrane vesicles from a biological sample, comprising at least one step during which the biological sample is treated by anion exchange chromatography on a support selected from cellulose, poly(styrene-divinylbenzene), silica, acrylamide, agarose, dextran, ethylene glycol-methacrylate co-polymer, alone or in mixtures, optionally functionalised.

In addition, to improve the chromatographic resolution, within the scope of the invention, it is preferable to use supports in bead form. Ideally, these beads have a homogeneous and calibrated diameter, with a sufficiently high porosity to enable the penetration of the objects under chromatography (i.e. the exosomes). In this way, given the diameter of exosomes (generally between 50 and 100 nm), to apply the invention, it is preferable to use high porosity gels, particularly between 10 nm and 5 $\mu$m, more preferably between approximately 20 nm and approximately 2 $\mu$m, even more preferably between about 100 nm and about 1 $\mu$m.

For the anion exchange chromatography, the support used must be functionalised using a group capable of interacting with an anionic molecule. Generally, this group is composed of an amine which may be ternary or quaternary, which defines a weak or strong anion exchanger, respectively.

Within the scope of this invention, it is particularly advantageous to use a strong anion exchanger. In this way, according to the invention, a chromatography support as described above, functionalised with quaternary amines, is used. Therefore, according to a more specific embodiment of the invention, the anion exchange chromatography is performed on a support functionalised with a quaternary amine. Even more preferably, this support should be selected from poly(styrene-divinylbenzene), acrylamide, agarose, dextran and silica, alone or in mixtures, and functionalised with a quaternary amine.

Examples of supports functionalised with a quaternary amine include the gels SOURCEQ. MONO Q, Q SEPHAROSE®, POROS® HQ and POROS® QE, FRACTOGEL®TMAE type gels and TOYOPEARL SUPER®Q gels.

A particularly preferred support to perform the anion exchange chromatography comprises poly(styrene-divinylbenzene). An example of this type of gel which may be used within the scope of this invention is SOURCE Q gel, particularly SOURCE 15 Q (Pharmacia). This support offers the advantage of very large internal pores, thus offering low resistance to the circulation of liquid through the gel, while enabling rapid diffusion of the exosomes to the functional groups, which are particularly important parameters for exosomes given their size.

The biological compounds retained on the column may be eluted in different ways, particularly using the passage of a saline solution gradient of increasing concentration, e.g. from 0 to 2 M. A sodium chloride solution may particularly be used, in concentrations varying from 0 to 2 M, for example. The different fractions purified in this way are detected by measuring their optical density (OD) at the column outlet using a continuous spectro-photometric reading. As an indication, under the conditions used in the examples, the fractions comprising the membrane vesicles were eluted at an ionic strength comprised between approximately 350 and 700 mM, depending on the type of vesicles.

Different types of columns may be used to perform this chromatographic step, according to requirements and the volumes to be treated. For example, depending on the preparations, it is possible to use a column from approximately 100 $\mu$l up to 10 ml or greater. In this way, the supports available have a capacity which may reach 25 mg of proteins/ml, for example. For this reason, a 100 $\mu$l column has a capacity of approximately 2.5 mg of proteins which, given the samples in question, allows the treatment of culture supernatants of approximately 2 l (which, after concentration by a factor of 10 to 20, for example, represent volumes of 100 to 200 ml per preparation). It is understood that higher volumes may also be treated, by increasing the volume of the column, for example.

In addition, to perform this invention, it is also possible to combine the anion exchange chromatography step with a gel permeation chromatography step. In this way, according to a specific embodiment of the invention, a gel permeation chromatography step is added to the anion exchange step, either before or after the anion exchange chromatography step. Preferably, in this embodiment, the permeation chromatography step takes place after the anion exchange step. In addition, in a specific variant, the anion exchange chromatography step is replaced by the gel permeation chromatography step. The present application demonstrates that membrane vesicles may also be purified using gel permeation liquid chromatography, particularly when this step is combined with an anion exchange chromatography or other treatment steps of the biological sample, as described in detail below.

To perform the gel permeation chromatography step, a support selected from silica, acrylamide, agarose, dextran, ethylene glycol-methacrylate co-polymer or mixtures thereof, e.g., agarose-dextran mixtures, are preferably used. As an illustration, for gel permeation chromatography, a support such as SUPERDEX®200HR (Pharmacia), TSK G6000 (TosoHaas) or SEPHACRYL® S (Pharmacia) is preferably used.

The process according to the invention may be applied to different biological samples. In particular, these may consist of a biological fluid from a subject (bone marrow, peripheral blood, etc.), a culture supernatant, a cell lysate, a pre-purified solution or any other composition comprising membrane vesicles.

In this respect, in a specific embodiment of the invention, the biological sample is a culture supernatant of membrane vesicle-producing cells.

In addition, according to a preferred embodiment of the invention, the biological sample is treated, prior to the chromatography step, to be enriched with membrane vesicles (enrichment stage). In this way, in a specific embodiment, this invention relates to a method of preparing membrane vesicles from a biological sample, characterised in that it comprises at least:

b) an enrichment step, to prepare a sample enriched with membrane vesicles, and c) a step during which the sample is treated by anion exchange chromatography and/or gel permeation chromatography.

According to a preferred embodiment, the biological sample is a culture supernatant treated so as to be enriched with membrane vesicles. In particular, the biological sample may be composed of a pre-purified solution obtained from a culture supernatant of a population of membrane vesicle-producing cells or from a biological fluid, by treatments such as centrifugation, clarification, ultrafiltration, nanofiltration and/or affinity chromatography, particularly with clarification and/or ultrafiltration and/or affinity chromatography.

Therefore, a preferred method of preparing membrane vesicles according to this invention more particularly comprises the following steps:

a) culturing a population of membrane vesicle (e.g. exosome) producing cells under conditions enabling the release of vesicles, b) a step of enrichment of the sample in membrane vesicles, and c) an anion exchange chromatography and/or gel permeation chromatography treatment of the sample.

As indicated above, the sample (e.g. supernatant) enrichment step may comprise one or more centrifugation, clarification, ultrafiltration, nanofiltration and/or affinity chromatography steps on the supernatant. In a first specific embodiment, the enrichment step comprises (i) the elimination of cells and/or cell debris (clarification), possibly followed by (ii) a concentration and/or affinity chromatography step. In an other specific embodiment, the enrichment step comprises an affinity chromatography step, optionally preceded by a step of elimination of cells and/or cell debris (clarification). A preferred enrichment step according to this invention comprises (i) the elimination of cells and/or cell debris (clarification), (ii) a concentration and (iii) an affinity chromatography.

The cells and/or cell debris may be eliminated by centrifugation of the sample, for example, at a low speed, preferably below 1000 g, between 100 and 700 g, for example. Preferred centrifugation conditions during this step are approximately 300 g or 600 g for a period between 1 and 15 minutes, for example.

The cells and/or cell debris may also be eliminated by filtration of the sample, possibly combined with the centrifugation described above. The filtration may particularly be performed with successive filtrations using filters with a decreasing porosity. For this purpose, filters with a porosity above 0.2 $\mu$m, e.g. between 0.2 and 10 $\mu$m, are preferentially used. It is particularly possible to use a succession of filters with a porosity of 10 $\mu$m, 1 $\mu$m, 0.5 $\mu$m followed by 0.22 $\mu$m.

A concentration step may also be performed, in order to reduce the volumes of sample to be treated during the chromatography stages. In this way, the concentration may be obtained by centrifugation of the sample at high speeds, e.g. between 10,000 and 100,000 g, to cause the sedimentation of the membrane vesicles. This may consist of a series of differential centrifugations, with the last centrifugation performed at approximately 70,000 g. The membrane vesicles in the pellet obtained may be taken up with a smaller volume and in a suitable buffer for the subsequent steps of the process.

The concentration step may also be performed by ultrafiltration. In fact, this ultrafiltration allows both to concentrate the supernatant and perform an initial purification of the vesicles. According to a preferred embodiment, the biological sample (e.g., the supernatant) is subjected to an ultrafiltration, preferably a tangential ultrafiltration. Tangential ultrafiltration consists of concentrating and fractionating a solution between two compartments (filtrate and retentate), separated by membranes of determined cut-off thresholds. The separation is carried out by applying a flow in the retentate compartment and a transmembrane pressure between this compartment and the filtrate compartment. Different systems may be used to perform the ultrafiltration, such as spiral membranes (Millipore, Amicon), flat membranes or hollow fibres (Amicon, Millipore, Sartorius, Pall, GF, Sepracor). Within the scope of the invention, the use of membranes with a cut-off threshold below 1000 kDa, preferably between 300 kDa and 1000 kDa, or even more preferably between 300 kDa and 500 kDa, is advantageous.

The affinity chromatography step can be performed in various ways, using different chromatographic support and material. It is advantageously a non-specific affinity chromatography, aimed at retaining (i.e., binding) certain contaminants present within the solution, without retaining the objects of interest (i.e., the exosomes). It is therefore a negative selection. Preferably, an affinity chromatography on a dye is used, allowing the elimination (i.e., the retention) of contaminants such as proteins and enzymes, for instance albumin, kinases, deshydrogenases, clotting factors, interferons, lipoproteins, or also co-factors, etc. More preferably, the support used for this chromatography step is a support as used for the ion exchange chromatography, functionalised with a dye. As specific example, the dye may be selected from Blue SEPHAROSE®(Pharmacia), YELLOW 86, GREEN 5 and BROWN 10 (Sigma). The support is more preferably agarose. It should be understood that any other support and/or dye or reactive group allowing the retention (binding) of contaminants from the treated biological sample can be used in the instant invention.

In a specific embodiment of the invention, the biological sample is obtained by subjecting a membrane vesicle-producing cell culture supernatant to at least one filtration stage.

In another specific embodiment of the invention, the biological sample is obtained by subjecting a membrane vesicle-producing cell culture supernatant to at least one centrifugation step.

In a preferred embodiment of the invention, the biological sample is obtained by subjecting a membrane vesicle-producing cell culture supernatant to at least one ultrafiltration step.

In another preferred embodiment of the invention, the biological sample is obtained by subjecting a membrane vesicle-producing cell culture supernatant to at least one affinity chromatography step.

A more specific preferred membrane vesicle preparation process within the scope of this invention comprises the following steps:

a) the culture of a population of membrane vesicle (e.g. exosome) producing cells under conditions enabling the release of vesicles, b) the treatment of the culture supernatant with at least one ultrafiltration or affinity chromatography step, to produce a biological sample enriched with membrane vesicles (e.g. with exosomes), and c) an anion exchange chromatography and/or gel permeation chromatography treatment of the biological sample.

In a preferred embodiment, step b) above comprises a filtration of the culture supernatant, followed by an ultrafiltration, preferably tangential.

In another preferred embodiment, step b) above comprises a clarification of the culture supernatant, followed by an affinity chromatography on dye, preferably on Blue SEPHAROSE®.

In addition, after step c), the material harvested may, if applicable, be subjected to one or more additional treatment and/or filtration stages d), particularly for sterilisation purposes. For this filtration treatment stage, filters with a diameter less than or equal to 0.3 $\mu$m are preferentially used, or even more preferentially, less than or equal to 0.25 $\mu$m. Such filters have a diameter of 0.22 $\mu$m, for example.

After step d), the material obtained is, for example, distributed into suitable devices such as bottles, tubes, bags, syringes, etc., in a suitable storage medium. The purified vesicles obtained in this way may be stored cold, frozen or used extemporaneously.

Therefore, a specific preparation process within the scope of the invention comprises at least the following steps:
   c) an anion exchange chromatography and/or gel permeation chromatography treatment of the biological sample, and
   d) a filtration step, particularly sterilising filtration, of the material harvested after stage c).

In a first variant, the process according to the invention comprises:
   c) an anion exchange chromatography treatment of the biological sample, and
   d) a filtration step, particularly sterilising filtration, on the material harvested after step c).

In another variant, the process according to the invention comprises:
   c) a gel permeation chromatography treatment of the biological sample, and
   d) a filtration step, particularly sterilising filtration, on the material harvested after step c).

According to a third variant, the process according to the invention comprises:
   c) an anionic exchange treatment of the biological sample followed or preceded by gel permeation chromatography, and
   d) a filtration step, particularly sterilising filtration, on the material harvested after step c).

Figure 2:
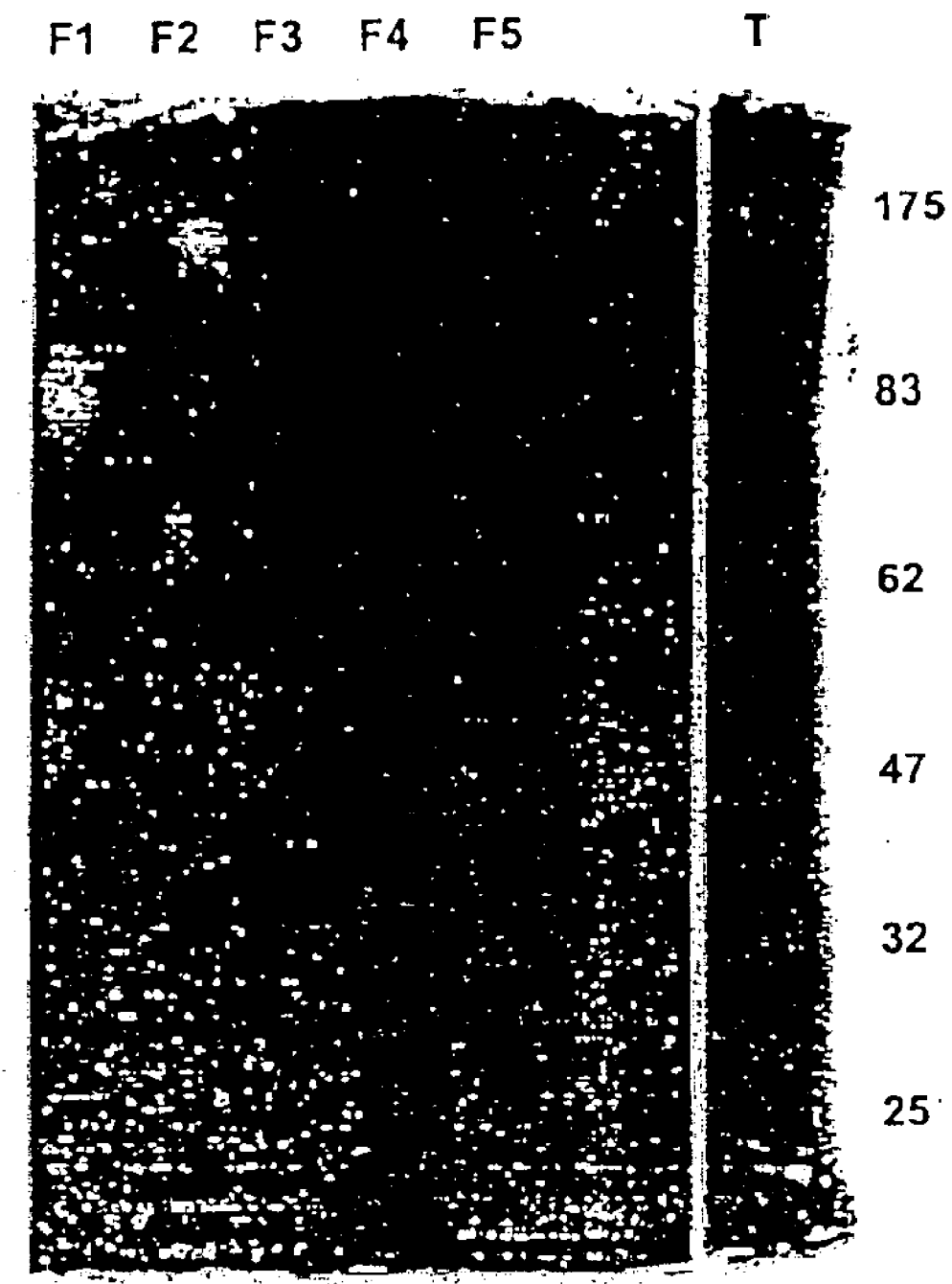

The results given in the examples demonstrate that the injection of an exosome preparation into the chromatography column allows to obtain symmetric absorption peaks, which are perfectly resolved (FIG. 1). The different fractions isolated in this way may be analysed using conventional protein electrophoresis techniques in denaturing gel followed by COOMASSIE® blue staining techniques or specific protein detection techniques using antibodies. It is thus possible to demonstrate, for texosomes, that the peak eluted in anion exchange chromatography with a 400 mM saline solution has an identical protein profile to that of an exosome preparation prepared using conventional methods (FIG. 2). In fact, this allows to characterise the peaks eluted at lower or higher saline concentrations as related to distinct, biological contaminants. In another experiment, membrane vesicles produced from dendritic cells (dexosomes) or certain texosomes are eluted at a ionic strength comprised between about 500 and 700 mM, and mastocyte-derived vesicles at about 350 mM.

Figure 3:
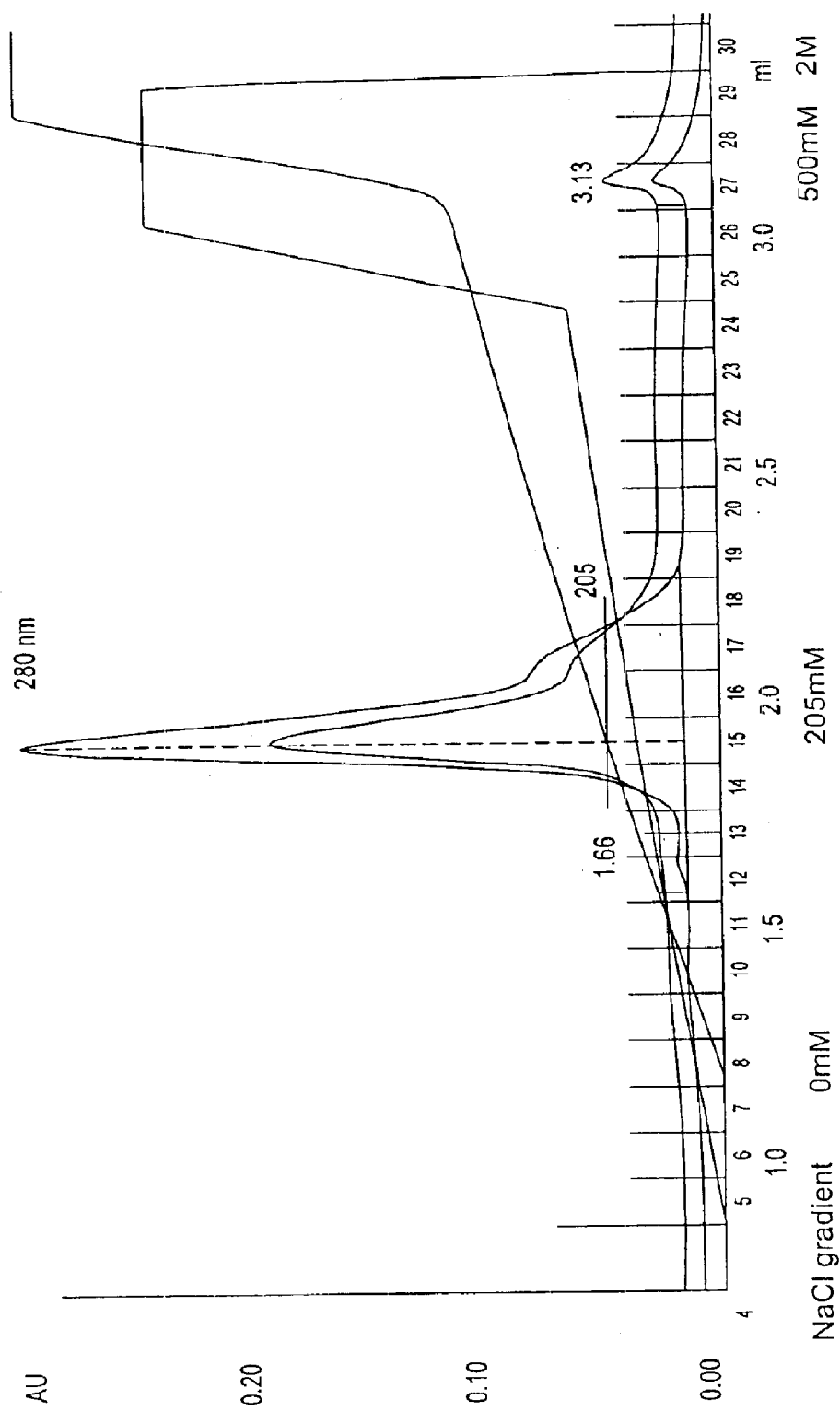

Furthermore, the results given in the examples also demonstrate that the method according to the invention allows the detection of the possible contamination of the preparation by major proteins of the culture medium such as bovine serum albumin. Indeed, the chromatography of a standard bovine serum albumin solution under the above conditions demonstrates a peak eluted at a distinct saline concentration from that of the exosomes (FIG. 3).

Therefore, the process according to the invention allows to (i) purify membrane vesicles under quality and quantity conditions compatible with pharmacological use, and (ii) detect the existence of distinct biological contaminants in the biological sample treated.

The process according to the invention may be applied to the preparation of membrane vesicles of varied origins. In particular, these vesicles may consist of exosomes produced by antigen presenting cells or by tumour cells, for instance. In addition, they may consist of primary cells, for example in culture, or of established lines; e.g., immortalised membrane vesicle-producing lines. They may consist of cells of Mammalian origin, particularly of murine or human origin.

In a specific embodiment of the invention, the membrane vesicles are vesicles produced by antigen presenting cells, particularly dendritic cells, B lymphocytes, macrophages and mastocytes, optionally after sensitisation of these cells to one or more selected antigens. A particularly preferred application of this invention is based on the preparation of membrane vesicles produced by dendritic cells. These may be human or animal dendritic cells, particularly of human or murine origin. These cells may be primary cells, harvested from a subject's biological fluids or produced ex vivo from precursor cells, or also from established line cells, immortalised with an oncogene, for example (EP 701 604).

A specific object of this invention resides in a method of preparing membrane vesicles (dexosome), characterised in that it comprises the following steps
   a) obtaining a population of dendritic cells,
   b) culturing the dendritic cells under conditions enabling the production of membrane vesicles (dexosomes), and
   c) purifying the membrane vesicles (dexosomes) using a process comprising at least an anion exchange chromatography treatment as described above.

A more preferred embodiment resides in a method of preparing dexosomes, comprising the following steps:
   a) obtaining a population of dendritic cells,
   b) culturing the dendritic cells under conditions enabling the production of dexosomes,
   c) treating the culture supernatant to produce a biological sample enriched with dexosomes, particularly with an ultrafiltration or an affinity chromatography step, and
   d) purifying the dexosomes using a process comprising at least an anion exchange and/or gel permeation chromatography stage, under the conditions described above.

More specifically, for the performance of this variant of the invention, the dendritic cells are preferentially obtained from a biological sample from a subject, e.g. bone marrow or peripheral blood.

In this respect, dendritic cell production techniques have been described in the prior art and may be used by the skilled artisan (see particularly the techniques described in the application WO99/03499, incorporated to this application by reference). The dendritic cells may thus be prepared from immune system stem cells, monocyte precursors or be isolated directly in a differentiated state (Review by Hart, Blood 90 (1997) 3245).

A preferred methodology within the scope of this invention is based on the production of dendritic cells from monocyte precursors or bone marrow. More specifically, within the scope of this invention, it is preferred to use dendritic cells obtained by treating monocyte precursors (contained in blood or marrow) in the presence of a GM-CSF+IL-4 or GM-CSF+IL-13 combination.

In addition, for the performance of this invention, it is particularly advantageous to use a population of dendritic cells comprising immature dendritic cells. Advantageously, a population of dendritic cells composed mainly (i.e. at least 60%, preferably 70%) of immature dendritic cells is used.

Therefore, the dendritic cell preparation step may advantageously comprise the preparation of a dendritic cell population comprising immature dendritic cells, particularly of human origin, especially from monocyte precursors, more specifically by treatment with a combination of cytokines such as GM-CSF+IL-4 or GM-CSF+IL-13.

In addition, within the scope of this invention, it is also possible to use immortalised dendritic cell populations. These may consist of immortalised dendritic cell lines (e.g. D1 line or any other line produced by introducing the myc oncogene in the dendritic cells, for example). They may also consist of dendritic cells prepared and immortalised in vitro. The interest of immortalised dendritic cells lies in the constitution of banks of cells sensitised to given antigen groups, which may be used industrially to prepare dexosomes compatible for administration to entire families of patients.

To produce the membrane vesicles (dexosomes), the dendritic cells may be simply cultured under conventional conditions known to those skilled in the field. However, it is preferred to culture these cells under conditions stimulating the production of dexosomes, particularly in the presence of factors capable of stimulating dexosome production, particularly a cytokine such as gamma interferon, interleukin 10 or interleukin 12 (e.g. see application WO99/03499). In a preferred embodiment of the process according to the invention, the dendritic cells are cultured, during step b) described above, under conditions stimulating membrane vesicle production.

Moreover, in a specific variant, the dendritic cells are sensitised to an antigen prior to membrane vesicle production. This embodiment allows the concentration of dendritic cells with specific antigen(s), so as to produce dexosomes with a given immunogenicity. The sensitisation may be performed using different well-known techniques, comprising for example placing the cells in contact with antigenic peptides, antigens, protein complexes, cells or membranes of cells expressing antigens, apoptotic bodies, membrane vesicles, liposomes, tumoral RNA or any nucleic acid coding for one or more antigens, antigenic determinants or epitopes (possibly carried by a viral or non-viral vector), etc. (e.g. see application WO99/03499). In a preferred method, the sensitisation is performed by incubation with peptides, antigens, RNA or nucleic acids. It is understood that this application is not limited to dendritic cell sensitisation or production techniques.

Another particularly advantageous embodiment of this invention is based on the preparation of membrane vesicles produced by tumoral cells, especially of human origin. In particular, they may consist of any cell from a solid or liquid tumour and cells transformed or immortalised in vitro. Solid, haematopoietic or ascitic tumours may be mentioned more preferentially.

A specific embodiment of this invention also resides in the preparation of membrane vesicles comprising one or more heterologous molecules, particularly recombinant molecules. In this way, it is possible, for example, to genetically modify membrane vesicle-producing cells (e.g., mastocyte lines), to make them express, in or at the surface of the vesicles they produce, molecules of interest (PCT/FR99/02691). This invention may also be used to purify such modified vesicles.

More generally, the invention may be applied to the preparation of membrane vesicles produced by any cell type, particularly exosome type vesicles, preferably with a diameter less than approximately 100 nm. These may consist of macrophage cells, mastocytes, reticulocytes, etc. In the experimental section, exosome preparations from (i) cell lines such as murine tumoral cell lines (TS/A), dendritic cell lines (D1), mastocyte cell line (RBL) and (ii) human monocyte-derived dendritic cells have been used. The results obtained can be transposed directly to other primary cultures such as human tumoral cells, dendritic cells, B lymphocytes, etc., cultivable under industrially acceptable conditions. The process according to the invention may thus be used in the purification of exosomes to be used in human treatment.

Depending on their origin, the membrane vesicles obtained in this way represent tools for the study of cancer or immune system regulation and for molecule transfer, antibody production, labelling, diagnosis, bank constitution, vaccine or medicinal product ingredients, etc.

In addition, the process according to the invention may also be used as a method for quality control on the possible presence of contaminants (particularly contaminating proteins) in the culture medium or in membrane vesicle preparations.

Therefore, in this respect, this invention may be applied both in a vesicle membrane preparation method and in an analytical system used to test the quality of a membrane vesicle preparation, irrespective of the preparation method.

Therefore, this invention also relates to a process to test for the presence of contaminants, particularly of protein or nucleic origin, in a membrane vesicle, particularly exosome, preparation, comprising subjecting a fraction of said preparation to at least an anion exchange chromatography and the detection of the presence of contaminants.

The invention also relates to, as a general rule, the use of anion exchange chromatography, particularly high performance liquid chromatography, for the preparation or purification of membrane vesicles. It also relates to the use of affinity chromatography for the preparation or purification of membrane vesicles.

The invention also relates to the membrane vesicles prepared using the process according to the invention, and any composition comprising such vesicles.

This invention will be described more completely using the following examples which must be considered as illustrative and not restrictive.

LEGEND TO THE FIGURES

FIG. 1: Elution profile after anion exchange chromatography of a sample of exosomes prepared by differential centrifugation.

FIG. 2: Protein profile analysis, by electrophoresis in SDS PAGE followed by COOMASSIE®blue staining, of the different elution fractions of an exosome preparation.

FIG. 3: Elution profile after anion exchange chromatography of a standard bovine serum albumin.

Figure 4:
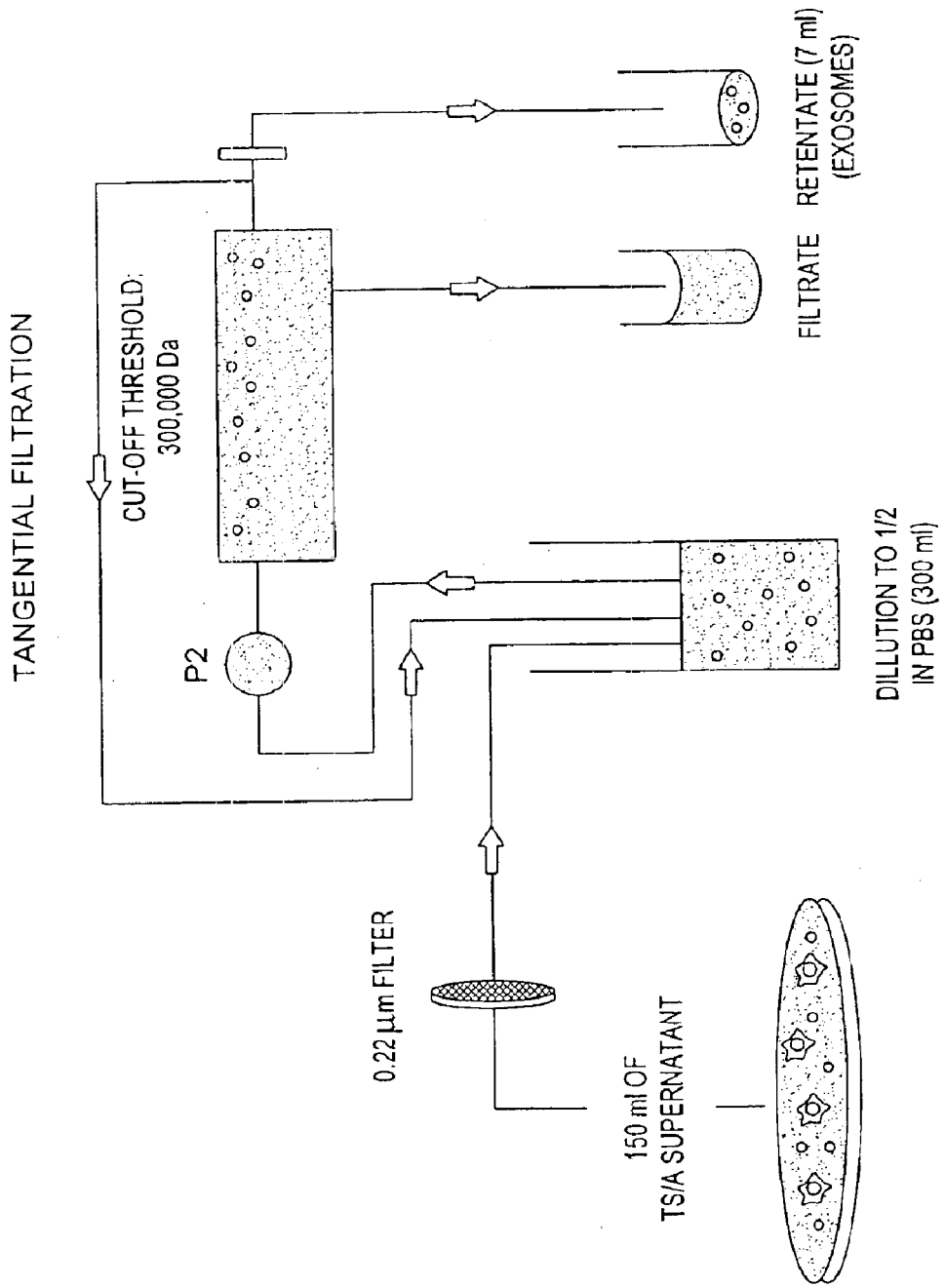

FIG. 4: Tangential ultrafiltration treatment diagram of a biological sample comprising membrane vesicles.

Figure 5:
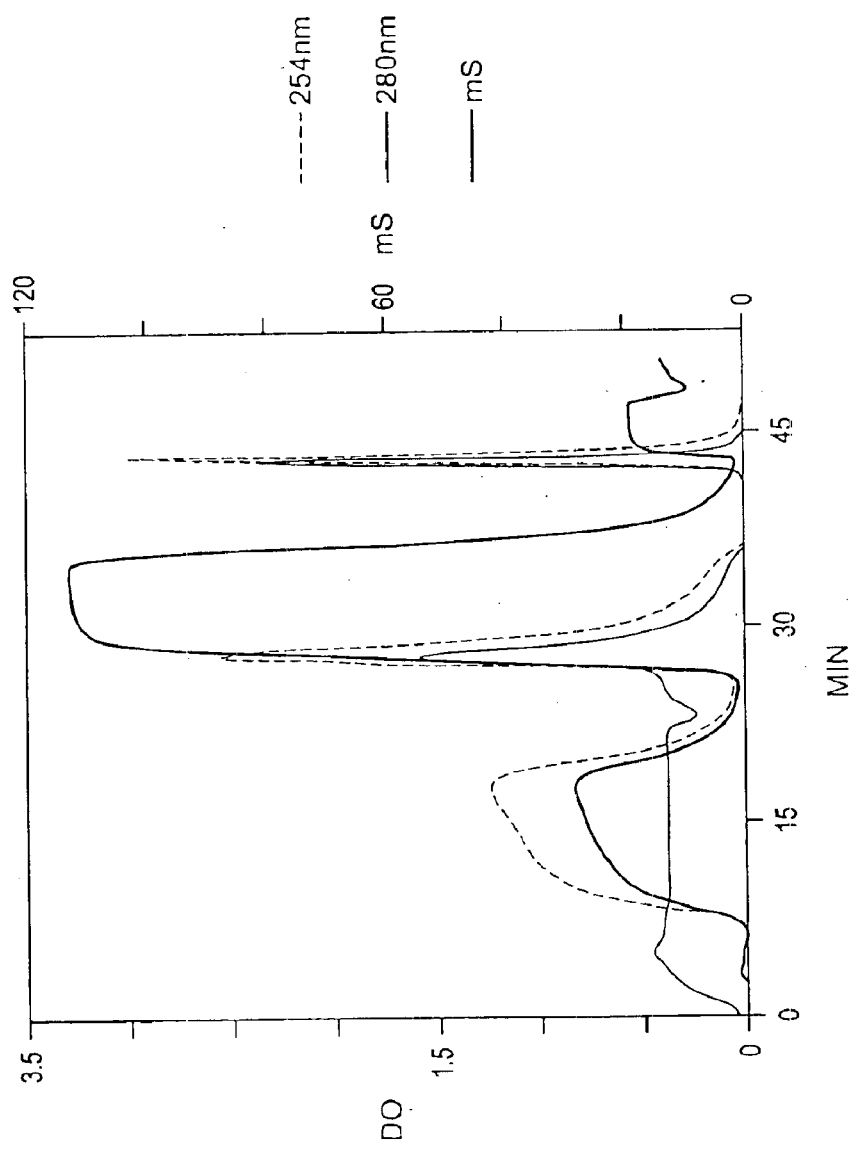

FIG. 5: General profile of the Blue SEPHAROSE® 6 FAST FLOW step, following 600 and 10 000 g centrifugations of a dexosome supernatant.

Figure 6:
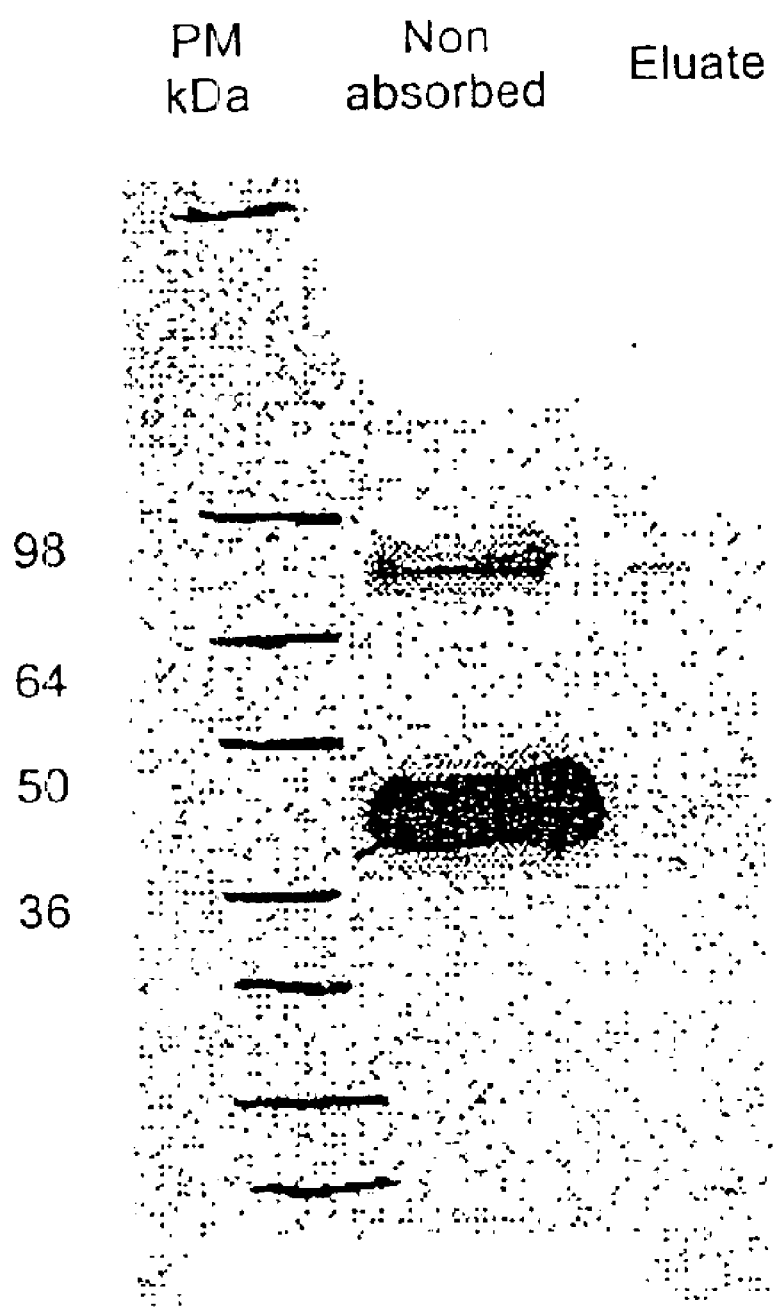

FIG. 6: Western blot against MHCII molecules of the exosomes, in the non-adsorbed fraction and the eluate of the Blue SEPHAROSE® 6 FAST FLOW step.

Figure 7:
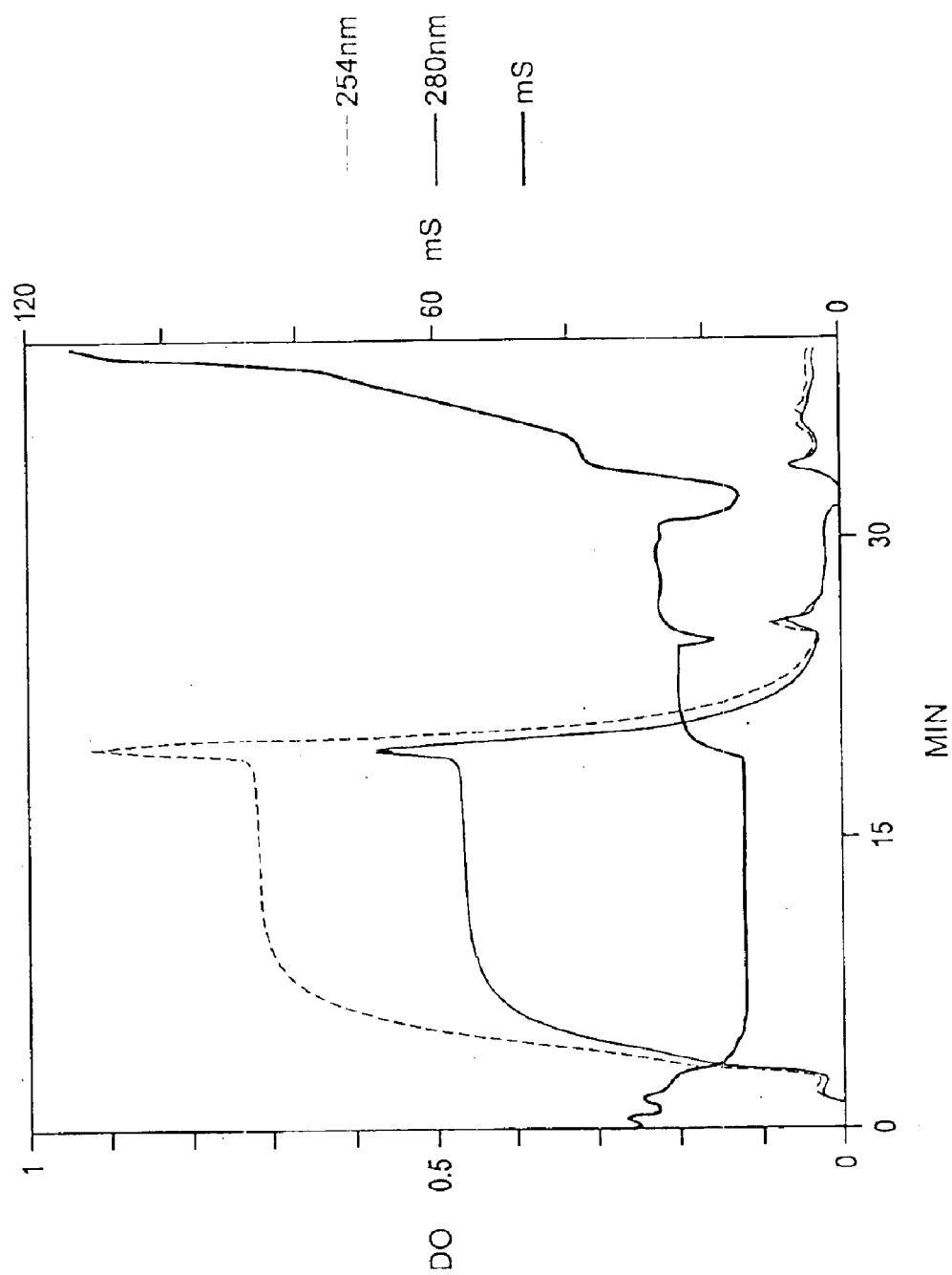

FIG. 7: General profile of the SOURCE Q 15 step following a Blue SEPHAROSE® 6 FAST FLOW step.

Figure 8:
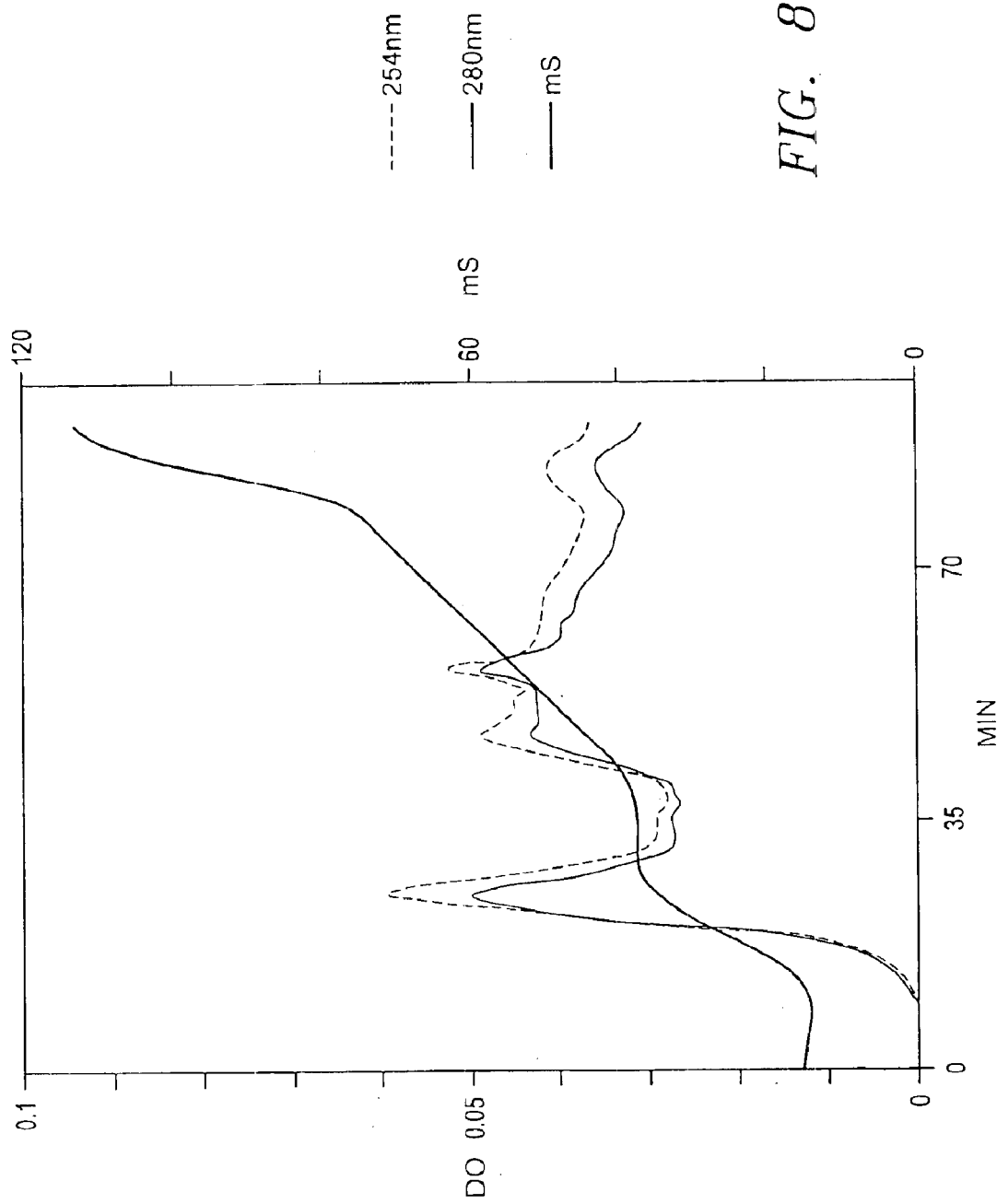

FIG. 8: Detail of the elution gradient on the SOURCE Q15 following a Blue SEPHAROSE® FAST FLOW 6 fast flow step (enlargement from bottom right of FIG. 7).

Figure 9:
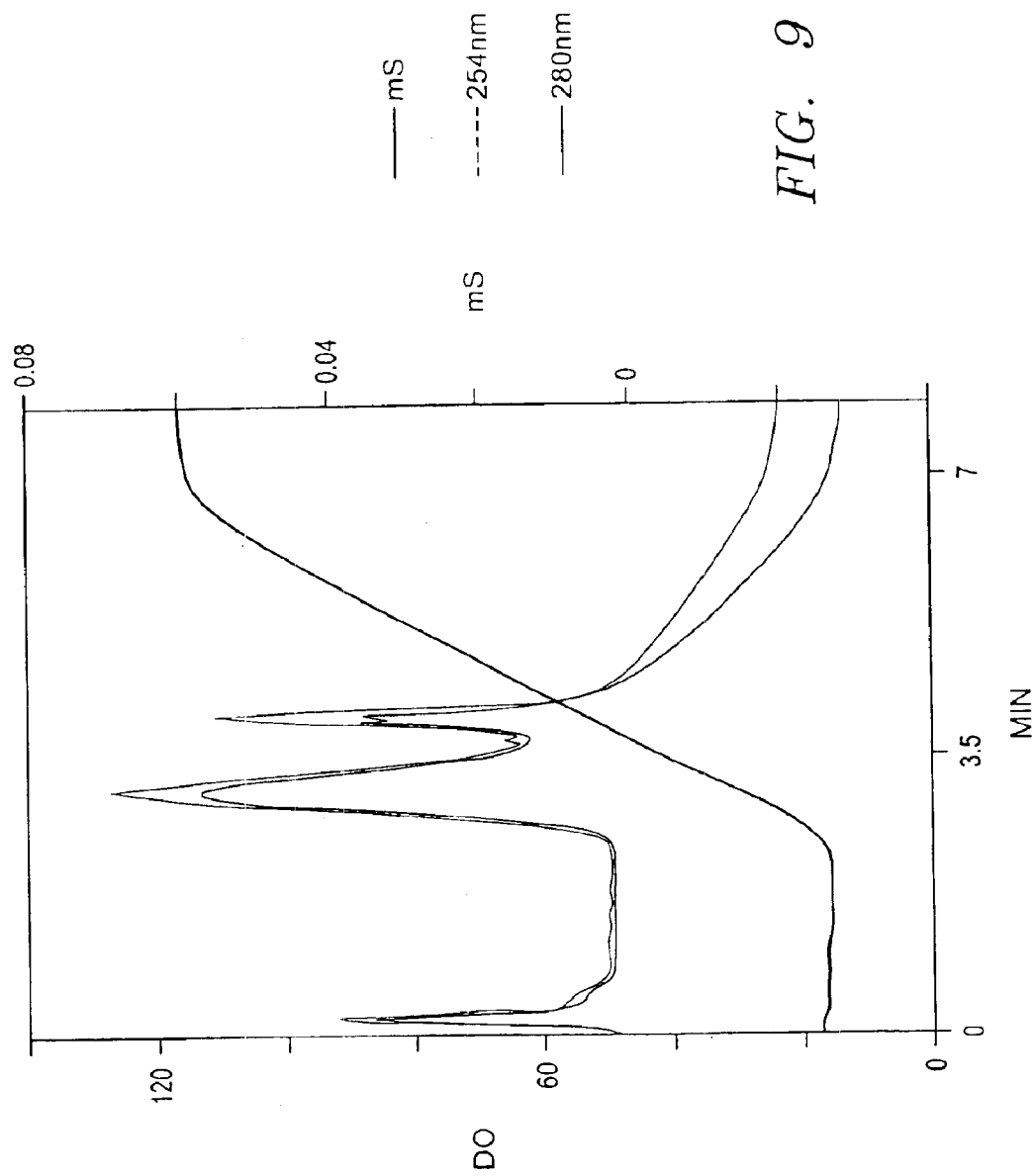

FIG. 9: Purification profile of exosomes produced by RBL DR+ cell line (eq. 53%1 g proteins) and purified on SOURCE Q15 column after Dnase and Rnase treatment.

Figure 10:
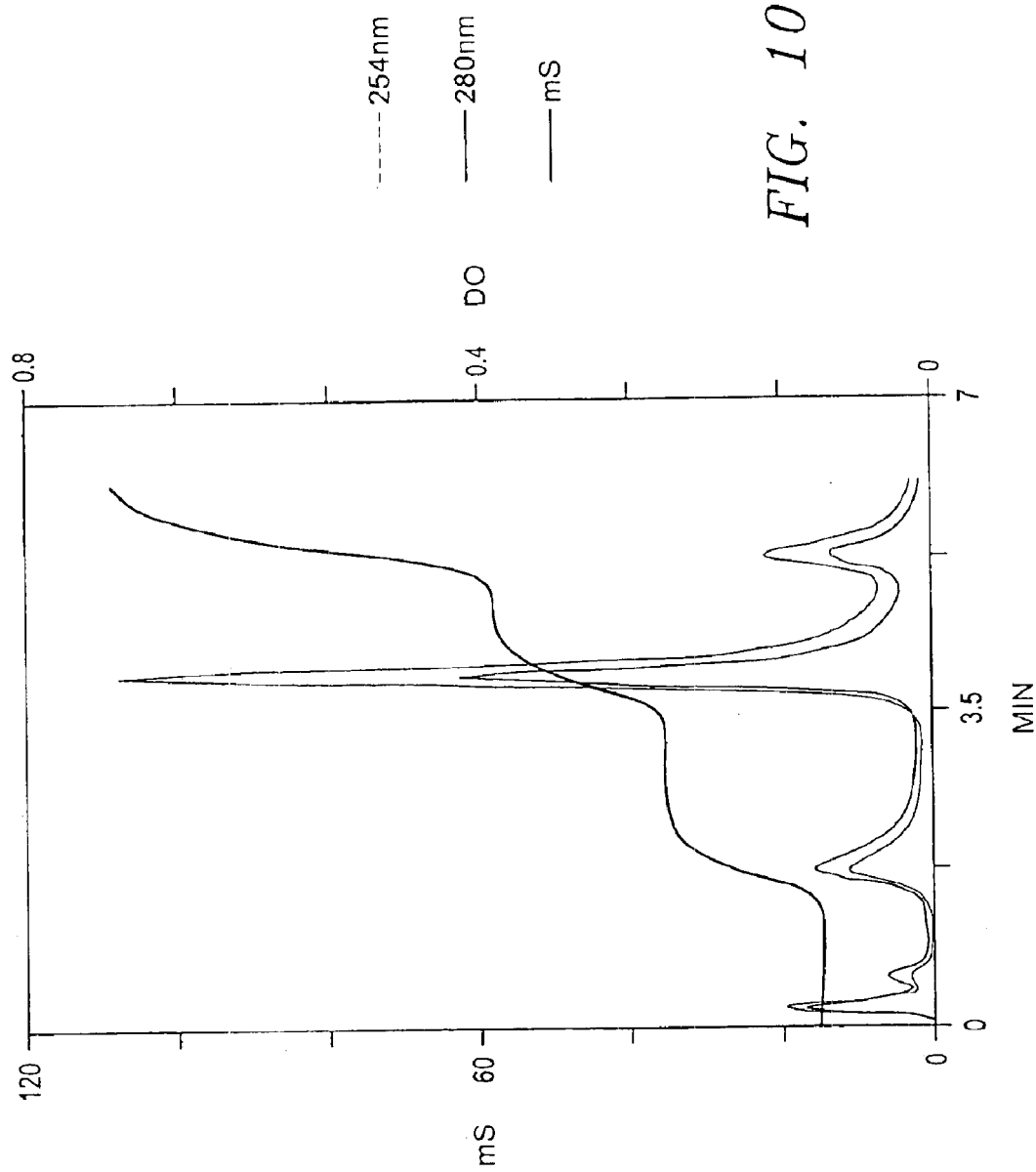

FIG. 10: Separation of exosomes by a discontinued NaCl gradient on a SOURCE Q15 support.

Figure 11:
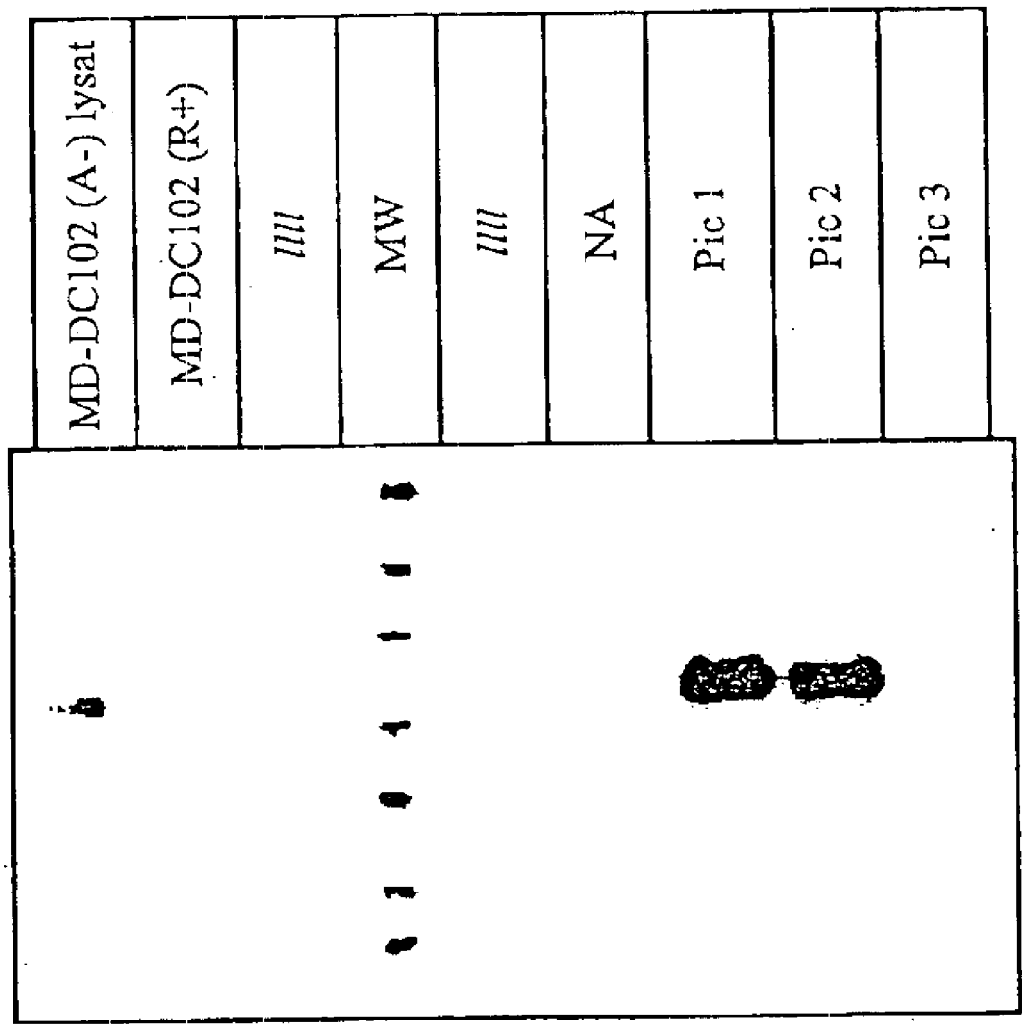

FIG. 11: Western blot against human MHCII molecules of each peak separated by HPLC and ultracentrifuged. Positive control: human dendritic cells expressing CMHII molecules. Negative control: ultracentrifuged medium (background signal). MW: molecular weight; NA: Non-Adsorbed fraction.

General Cell Culture and Molecular Biology Techniques

1) Cell cultures

The TS/A cell line is a murine cell line established from a spontaneous mammary carcinoma. This line is cultured at 37° C. in the presence of 5% $CO_2$ in RPMI medium in the presence of 10% foetal calf serum (Dominique Dutcher).

The dendritic cell lines are kept in an IMDM medium containing 10% inactivated foetal bovine serum, 2 mM of L-glutamine, 50 µM of 2-βME, 100 UI/ml of penicillin and 100 µg/ml of streptomycin.

2) SDS PAGE protein analysis

20 µl of sample is diluted in Laemmli buffer (Nature 227 (1970) p.680–685) and then subjected to thermal denaturation at 95° C. for 10 min and then loaded on 10% acrylamide gels (Novex 1 mm×10 wells). After migration, the gels are stained with COOMASSIE®blue.

EXAMPLES

1) ANION EXCHANGE CHROMATOGRAPHY OF AN EXOSOME PREPARATION PRODUCED BY TUMORAL CELLS (TS/A LINE): SDS PAGE PROTEIN PROFILE ANALYSIS OF THE DIFFERENT ELUTED FRACTIONS.

This example illustrates how an anion exchange chromatography treatment can be used to separate impurities from an exosome preparation.

1.1. Protocol:

In this experiment, the starting material is made up of a concentrate of exosomes prepared by differential centrifugation from a TS/A cell culture supernatant, used to separate the exosomes from the cells or cell debris present in the culture medium. The first centrifugation is performed at a low speed (300 g for 5 min) in order to cause the sedimentation of the cells in suspension present in the culture supernatant. Two other centrifugations (1200 g for 20 min followed by 10,000 g for 30 min) are carried out to cause the pelleting of the cell debris. The supernatant clarified in this way is then subjected to ultracentrifugation at a high speed of 70,000 g for 1 hour used to cause the sedimentation of the exosomes. This preparation is then washed in a large volume of saline solution to be recentrifuged under the above conditions. The pellet is then taken up with a volume of approximately 100 µl of saline solution and forms a concentrated exosome solution. The quantity of proteins is measured using the Bradford technique (Biorad, Ivry, France). This concentrate has a total protein content between 500 and 1000 µg/ml.

40 µg of this exosome preparation diluted in 500 µl of pH 8 50 mM HCl/Tris buffer is injected onto a column containing SOURCE Q 15 gel (Pharmacia) stabilised in a pH 8 50 mM HCl/Tris buffer. After rinsing, the adsorbed species are eluted on 30 volumes of column with a linear 0 to 500 mM NaCl gradient, followed by a 2 M NaCl solution. The elution fractions are analysed by spectrophotometry at 260 and 280 nm. The elution fractions are grouped into 5 major fractions (F1 to F5), to analyse their respective protein profile. The proteins of each fraction are precipitated with 1/10 volume of a 100% trichloroacetic acid solution and then rinsed with an acetone solution. The protein pellets are taken up with 20 µl of Laemmli solution and are deposited on an SDS PAGE acrylamide gel which is then stained with COOMASSIE®blue.

1.2. Results:

The elution profiles at 260 and 280 nm are shown on FIG. 1. The profiles show the presence of 3 distinct symmetric peaks, eluted at the respective saline concentrations of 105 mM, 400 mM and 2 M NaCl.

The protein profile analysis of the fractions corresponding to the different peaks shows that the peak eluted at 400 mM NaCl has an identical protein profile to that of a conventional exosome preparation prepared by centrifugation (FIG. 2). The ratio between the absorptions at 260 and 280 nm measured at a value of 0.8 is compatible with that described for proteins.

However, the peak eluted (fraction F2) at 105 mM NaCl shows a different protein profile, revealing only two distinct bands. The absorbance measurements at 260 and 280 nm give a ratio of 1.6 suggesting the presence of a combination of nucleic acids and proteins.

The fraction F5 eluted at 2 M NaCl corresponds to the biological compounds strongly linked to the column.

It is therefore possible to separate exosome from impurities with an anion exchange step.

2) ANION EXCHANGE CHROMATOGRAPHY OF A STANDARD BOVINE SERUM ALBUMIN SOLUTION

This anion exchange chromatography technique can also be used to evaluate the degree of contamination of an exosome preparation by the proteins present in the culture medium. In this way, by performing chromatography on 10 µg of a bovine serum albumin solution, corresponding to the majority protein in the culture medium, we demonstrate that it is eluted at 205 mM NaCl in the form of a narrow peak distinguishable from the peaks described above for exosomes.

3) ULTRAFILTRATION TREATMENT OF A CULTURE SUPERNATANT CONTAINING EXOSOMES.

This example demonstrates that it is possible to concentrate exosomes by ultrafiltration. In addition, the exosomal preparation is low in contaminant proteins such as BSA.

Protocol: (FIG. 4)

150 ml of a cell culture supernatant obtained after centrifugation of TSA cells at 300 g is subjected to a filtration on a 0.22 µm porosity filter (Millipore). The filtrate is diluted by half in PBS. The resulting 300 ml is filtered tangentially with a filtration cassette (10 $cm^2$ of membrane) with a cut-off threshold of 300,000 D (Sartorius).

Results:

7 ml of retentate are obtained after 1 hour of filtration. The retentate was subjected to an ultracentrifugation (79,000) to cause the pelleting of and analyse the exosomes. An SDS-PAGE analysis followed by Coomassie blue staining revealed that the sample contained significantly less BSA than the solution which was ultrafiltered. In addition, specific protein bands of the exosomes produced from TSA are observed.

Therefore, ultrafiltration may be used in an exosome purification process in order to separate the exosomes from contaminating proteins.

4) PURIFICATION BY HPLC OF HUMAN EXOSOMES, PRODUCED BY HUMAN MONOCYTE-DERIVED DENDRITIC CELLS (MDDC)

4.1. Materials and Methods

Buffers and Stock Solutions 0.22 µm filtered stock solutions are used, except for the water and soda solution. The first buffer is a 100 mM (Sigma, 99% purity) Bis-Tris-Propane (BTP) solution, buffered to pH 6; this buffer is connected to channel A of the chromatograph (BioCad Sprint, Perkin-Elmer). The second buffer is a 100 mM Bis-Tris-Propane solution, buffered to pH 9; this buffer is connected to channel B of the chromatograph. The water is produced on resin with a MILLI-Q™system (Millipore) at a resistance of 18 MΩcm. The water is connected to channel C. A 3 M sodium chloride stock solution (NaCl, Prolabo, 99.5% purity) is connected to channel D. A 0.1 M soda solution (NaOH, Prolabo, 98% purity minimum) is connected to channel F. Channel E is used to load the culture supernatants onto the columns.

All the buffers are produced from water produced by the MILLI-Q™ system and are not degassed.

Columns

Blue SEPHAROSE®6 FAST FLOW (Pharmacia): The first step is performed with a Blue SEPHAROSE® 6 FAST FLOW (Pharmacia) column. The matrix is agarose linked with Blue SEPHAROSE® 6 FAST FLOW Blue 3G (7%). The particle size is between 45 and 165 μm. The maximum linear flow rate is 750 cm/hour. The gel is stable at pH values between 4 and 12; at the extreme pH values, 4 and 12, the gel may be damaged, inducing a decrease in the fixing capacity (segregation of the Blue SEPHAROSE® 6 FAST FLOW 6 fast flow and an increase in pressure (fine formation).

Blue SEPHAROSE® 6 FAST FLOW is specific for compounds such as albumin, kinases, dehydrogenases and other enzymes containing cofactors such as $NAD^+$, clotting factors, interferons and lipoproteins.

The theoretical fixing capacity of Blue SEPHAROSE® 6 FAST FLOW is approximately 15 to 20 mg of serum albumin per ml of gel.

The column volume used is approximately 5.5 ml of gel (C10/10, Pharmacia), or a theoretical capacity of 80 to 110 mg of serum albumin. The flow rate used is 2 ml/min (150 cm/hour) on the BioCad Sprint and 3.5 ml/min (260 cm/hour) with a Pharmacia detection system.

The pressure does not exceed 2.5 bar and is essentially due to the OD measurement cells.

SOURCE 15Q:

The second step is performed with a SOURCE 15Q (Pharmacia) column, a strong anion exchanger. The matrix is polystyrene cross-linked with divinyl benzene. The bead size is 15 μm and homogeneous. The beads are passed through a system of pores with a size varying from 20 to 1000 nm. These gels are very resistant to pressure and withstand high linear flow rates (1800 cm/hour and over), while retaining a satisfactory resolution and capacity. This is made possible by the homogeneity of the beads and their porosity which increases the access of the molecules to the functional groups.

The gel is stable at pH values between 2 and 12, beyond which the gel is liable to undergo significant damage, reducing its capacities.

The theoretical fixing capacity of this exchanger is approximately 25 mg of proteins per ml of gel. A 0.8 ml column (PEEK column 4.6 mm ID/50 mm L, Perkin-Elmer) is used, giving a maximum capacity of 20 mg of proteins. The actual capacity, ensuring a good resolution, is approximately 10% of this maximum capacity, or 2 mg of proteins. The flow rate used is 5 ml/min (1880 cm/hour) and allows quick separations. The column is packed with the POROS®SELF PACK SYSTEM at 15 ml/min at 150 bar.

Chromatograph (BIOCAD SPRINT)

The BIOCAD is an HPLC (High Performance Liquid Chromatography) system which makes it possible to work at high pressures (maximum bar) and at flow rates ranging from 0.2 to 60 ml/min. Up to 6 buffers may be connected (the 6 channels are currently used) and the system may be treated with 0.1 M soda (pH 12) to depyrogenate the tubing and column.

The separations may be performed at ambient temperature or at 4° C. The samples are loaded either via one of the accessible channels or via injection loops for small volumes (100 μl to 5 ml). The detection system uses a double-channel UV cell: 190 to 450 nm for UV and 366 to 700 nm for visible. Conventionally, a 254 nm detection is used for nucleic acids and a 280 nm detection for proteins (it is the amino acids with a benzene cycle such as tyrosins, tryptophans and phenylamines that absorb). The system is entirely computerised (software developed by Perspective biosystem). For each separation, all the parameters (pressure, flow rate, conductivity, optical density, pH, etc.) can be monitored.

Finally, the separated sample is either recovered in a 50 ml FALCON TUBE or collected in siliconed EPPENDORF tubes (ADVANTEC SF-2120 collector) to minimise non-specific interactions.

Exosome Production from Dendritic Cells

Firstly, the dendritic cells are obtained from peripheral blood monocyte precursors. The isolated monocytes are cultured in the presence of a combination of GM-CSF and IL-13 or IL-4 (see the techniques described in the application WO99/03499). For the production of exosomes, it is preferable to use a population of immature dendritic cells.

4.2. Blue SEPHAROSE® 6 FAST FLOW

The culture supernatants are centrifuged twice at 600 g and once at 10,000 g before being loaded onto the Blue SEPHAROSE® 6 FAST FLOW column.

A 5.5 ml column is used, the flow rate is 2 ml/min (linear flow rate 150 cm/hour, contact time 2.7 min) and the pressure is approximately 2.5 bar (FIG. 5). The column is equilibrated in 12 mM BTP buffer (150 mM NaCl, pH 7). After equilibration, the supernatant is loaded onto the column which is then washed with the same equilibrating buffer until the O.D. drops. The fixed proteins are eluted in 12 mM BTP buffer (1.5 mM NaCl, pH 7) (in 3 to 4 column volumes). The column is regenerated by passing water (2 to 3 column volumes), followed by 2 volumes of 0.1 M soda (pH 12). Finally, the column is restabilised in 12 mM BTP (150 mM NaCl, pH 7).

Quantitative and qualitative aspect of the Blue SEPHAROSE® 6 FAST FLOW 6 stage.

As described above, the Blue SEPHAROSE® 6 FAST FLOW 6 stage is specific for proteins such as albumin which is a major contaminant of the culture supernatant. The protein concentration of each fraction of the Blue SEPHAROSE® 6 FAST FLOW stage is measured using a BIORAD technique (OD measurement at 600 nm). The results are given in table 1.

TABLE 1

Protein concentration in each fraction of the Blue SEPHAROSE ® 6 FAST FLOW stage.

|  | supernatant | Non-adsorbed | Elution peak | Regeneration peak |
| --- | --- | --- | --- | --- |
| Protein concentration (mg/ml) | 3.69 | 0.18 | 3.32 | 1.48 |
| Volume (ml) | 25 | 37.5 | 20 | 20 |

TABLE 1-continued

Protein concentration in each fraction of the Blue SEPHAROSE ® 6 FAST FLOW stage.

|  | supernatant | Non-adsorbed | Elution peak | Regeneration peak |
|---|---|---|---|---|
| total quantity of proteins (mg) | 92.2 | 6.7 | 66.4 | 29.6 |
| Yields (%) | 100 | 7.3 | 72 | 32.1 |

Most of the proteins are detected either in the eluate (72%) or in the regeneration (32%). The non-adsorbed fraction only represents 7 to 10% of the total proteins loaded onto the Blue SEPHAROSE® 6 FAST FLOW column. The stage is specific for the major contaminants of the supernatant. To check this specificity of Blue SEPHAROSE® 6 FAST FLOW, each fraction is deposited on an SDS-PAGE gel under reducing conditions and stained with silver nitrate. The overload of the column (50 ml supernatant loaded onto a 5.5 ml Blue SEPHAROSE® 6 FAST FLOW 6 ft flow column) was used to calculate the maximum quantity of proteins of the culture supernatant that it is possible to load onto the column per ml of gel (table 2). In this case, the percentage of the non-adsorbed fraction increases from 7 to over 30% of the quantity of protein loaded. This value is between 16 and 18 mg of proteins per ml of Blue SEPHAROSE® 6 FAST FLOW 6 fat flow gel. In conclusion, 1 ml of Blue SEPHAROSE® 6 FAST FLOW 6 gel allows the purification of approximately 5 to 6 ml of culture supernatant (2.5% HSA AIMV). This value is very important for the scale-up study since it determines the size of the column to use and, consequently, the cost of this stage.

TABLE 2

Overload study of the Blue SEPHAROSE ® 6 FAST FLOW stationary phase in the first stage.

|  | Supernatant | Non-adsorbed | Elution peak | Regeneration peak |
|---|---|---|---|---|
| Protein concentration (mg/ml) | 3.02 | 0.87 | 3 | 1.56 |
| Volume (ml) | 50 | 60 | 20 | 20 |
| total quantity of proteins (mg) | 151 | 52.2 | 60 | 31.2 |
| Yields (%) | 100 | 34.6 | 39.7 | 20.6 |

As expected, the major contaminant of the culture supernatants, after the 600 and 10,000 g centrifugations, is albumin. After fixing on the Blue SEPHAROSE®6 FAST FLOW this contaminant is detected in the eluate and regeneration fractions. In addition to this contaminant, many other low and high molecular weight contaminants are detected.

The Blue SEPHAROSE® 6 FAST FLOW 6 fast flow stage enables the elimination of approximately 90 to 95% of the culture supernatant contaminants. The exosomes are found in the non-adsorbed fraction of the Blue SEPHAROSE® 6 FAST FLOW (FIG. 6).

4.3. Anion exchanger step: SOURCE 15Q (Pharmacia).

A 0.8 ml SOURCE 15Q column is used with a 5 ml/min flow rate (linear flow rate1880 cm/hour, contact time 0.1 min) with a pressure of approximately 50 bar. The non-adsorbed fraction of the Blue SEPHAROSE® 6 FAST FLOW is loaded directly onto the SOURCE 15Q (FIG. 7) with no modifications in the saline (NaCl) concentration or the pH.

After the binding stage, the column is washed in 12 mM BTP buffer (280 mM NaCl) at pH 7 (35 column volumes) until the OD drops to values close to 0. A second washing stage is performed at a 150 mM NaCl saline concentration (10 column volumes) to reinforce the interactions of the exosomes with the support (stationary phase).

A first gradient from 150 to 420 mM NaCl in 7 column volumes (FIG. 8) is carried out and the gradient is then stopped for 9 column volumes. The second gradient starts from 420 mM NaCl to 1 M NaCl in 25 column volumes. The exosomes are eluted in the second gradient in two peaks at 550 and 700 mM NaCl (FIG. 8). The column is regenerated by passing 10 column volumes of water followed by 10 column volumes of 0.1 M soda (pH 12) and, finally, by passing 10 column volumes of 3 M NaCl. The column is then equilibrated in 12 mM BTP buffer (150 mM NaCl, pH 7).

Quantitative and qualitative aspects of the SOURCE 15Q stage.

As illustrated in FIG. 6, most of the proteins of the non-adsorbed Blue SEPHAROSE®6 FAST FLOW 6 fraction are not retained on the column. The protein concentrations were measured using a BIORAD test (OD absorption at 600 nm) and are summarised in table 3.

TABLE 3

Quantitative aspects of the SOURCE 15Q stage after a Blue SEPHAROSE ® 6 FAST FLOW stage.

|  | Start (non-adsorbed Blue sepharose 6 fast flow) | Non-adsorbed source 15Q | Eluate fractions 4 to 6 | Eluate fractions 19 to 23 |
|---|---|---|---|---|
| Proteins (mg/ml) | 0.17 | 0.14 | 0.01 | 0.02 |
| Volume (ml) | 85 | 98 | 3 | 5 |
| Total proteins (mg) | 14.45 | 13.72 | 0.03 | 0.10 |
| Yields (%) | 100 | 94.9 | 0.2 | 0.8 |

95% of the proteins loaded on the SOURCE 15Q column are not retained. The pooled fractions 4 to 6 and the pooled fractions 19 to 23 represent approximately 1.5%. The regeneration was not assayed. The yield is very close to 100%: all the loaded proteins and vesicles are eluted from the column. In terms of the column's protein concentration, SOURCE 15Q is capable of binding approximately 25 mg of proteins (manufacturer's data), corresponding to 20 mg of proteins for 0.8 ml columns. It is clear that these values are very far from the column's maximum and the 5 to 10% for a good resolution, since they range between 1 and 2 mg or proteins. Under these conditions, with a 0.8 ml SOURCE 15Q column, it is possible to purify between 200 and 400 ml of culture supernatant.

Each elution peak is ultracentrifuged (100,000 g for 1 hour) and pooled for electron microscope observation. The first peak (eluted between 150 and 420 mM NaCl) essentially contains proteins, cell debris and some vesicles labelled with an anti-MHC II antibody. The second peak (eluted at 550 mM NaCl), processed in the same way, shows a lower background noise and a much higher number of vesicles labelled with an anti MHC II antibody; the size of the vesicles is also heterogeneous.

The third peak (eluted at 700 mM NaCl) does not show any background noise, the vesicles are practically all labelled with an anti-MHC II antibody and are much more homogeneous in size.

These two fractions (peak 2 and 3) are to be compared to those obtained using the conventional ultracentrifugation purification process. In this case, a significant background noise and a considerable heterogeneity of the vesicles compared to the two chromatography peaks are observed. In addition, there appears to be a separation between the debris and the exosomes purified by HPLC which is not the case with ultracentrifugation.

4.4. Conclusions

In two chromatography stages, the first involving a negative selection (Blue SEPHAROSE® 6 FAST FLOW of exosomes and the second involving a positive selection and a selective elution of exosomes (SOURCE 15Q stage), approximately between 99 and 99.5% of the proteins in the culture supernatant are eliminated, while retaining the exosomes. The process preserves the integrity of the exosomes in electron microscopy. Therefore, this process is specific for exosome purification.

As an example, other columns retaining serum proteins may be used. In addition, cationic macroporous columns may be used instead of SOURCE 15 Q.

5) PURIFICATION BY HPLC OF EXOSOMES PRODUCED FROM THE RBL (RAT BASOPHILIC LEUKEMIA) LINE

The exosomes are produced from an RBL (Rat Basophilic Leukemia) line, transfected in a stable way to express, on the exosome membrane, human MHC II molecules (PCT/FR99/02691). After induction, with an ionophore (iomicyne), the cells degranulate and release exosomes in a protein-free medium (RPMI). After the cells are eliminated by centrifugation at 600 g for 10 min, the supernatants are recovered and treated with a DNase (Sigma) and an RNase (Sigma).

The treated supernatants are then centrifuged at 10,000 g at 37° C. for 30 min and then at 100,000 g for 1 hour.

The ultracentrifugation sediment is loaded onto an ion exchange column, SOURCE 15Q, (Pharmacia) (FIG. 9). A 0.8 ml column is used with a 5 ml/min flow rate (linear flow rate 1880 cm/hour, contact time 0.1 min).

The column is equilibrated in 12 mM BTP buffer (150 mM NaCl, pH 7). After loading the sample, the column is washed with 15 to 20 column volumes of the same equilibrating buffer. The elution is performed with 25 column volumes by varying the saline concentration from 150 mM to 1 M NaCl, the pH is kept constant (FIG. 9). The protein contamination of the medium is very low since the cells are washed in PBS and the induction and release of the exosomes are performed in RPMI only. This is confirmed by the absorption observed (280 and 254 nm) in the non-adsorbed fraction of SOURCE 15Q. The presence of the exosomes is confirmed by a Western Blot analysis targeted against MHC II molecules (FIG. 11) after separation of the peaks with steps in NaCl (FIG. 10) and ultracentrifugation of each of the peaks.

Three peaks plus one non-adsorbed fraction are observed: a first peak eluted at 350 mM NaCl, a second peak eluted at 700 mM NaCl and finally a third peak eluted at 1.5 M NaCl. The peak at 700 mM is the majority peak. In a Western Blot analysis targeted against human MHC II molecules, a signal is detected in peaks 1 (350 mM NaCl) and 2 (700 mM NaCl). It should be noted that peak 1, which has a protein signal intensity 7 to 8 times lower than peak 2, shows a Western Blot signal equivalent to that of peak 2. This may convey a higher purity of peak 1. To confirm this fact, the peaks were ultracentrifuged and observed in electron microscopy.

Peak 1 is very rich in exosomes labelled with an anti-human MHC II antibody and there is little or no background noise. The exosomes are heterogeneous in size and there does not appear to be a separation of the exosomes by their size but by a specific competition mechanism between the eluant (NaCl) and the exosomes.

The fractions between the two peaks were analysed by electron microscopy. Few exosomes were detected with a higher background noise than in peak 1.

Peak 2 is very similar to the fractions between the two peaks; few exosomes and a higher background noise are detected.

CONCLUSIONS

SOURCE 15Q is able to retain exosomes and separate them from potential contaminants (FIG. 9). The vast majority of the exosomes are eluted in the same peak at 350 mM NaCl. In electron microscopy, the exosomes appear "normal" with a specific label for human MHC II molecules. The heterogeneity of the size of the exosomes (peak 1) appears to indicate that the separation is based on ion exchanges and not on screening. Therefore, SOURCE 15Q may be used as a purification step for RBL exosomes.

What is claimed is:

1. A process of preparing membrane vesicles from the culture supernatant of a biological sample, wherein said biological sample comprises membrane vesicles produced by antigen presenting cells that have been sensitized to one or more selected antigens, said method comprising at least a filtration of the culture supernatant, followed by a tangential ultrafiltration to produce a biological sample enriched with membrane vesicles;

an anion exchange chromatography treatment performed under pressure of the enriched sample followed or preceded by gel permeation chromatography of said enriched sample; and a sterilizing filtration step.

2. Process according to claim 1, wherein said anion exchange chromatography is performed on a support functionalized with a quaternary amine.

3. Process according to claim 1, wherein the biological sample is selected from a biological fluid, a culture supernatant, a cell lysate and a pre-purified solution.

4. A process preparing membrane vesicles from a biological sample, wherein said process comprises at least:

a) the culture of a population of membrane vesicles producing antigen presenting cells under conditions enabling the release of vesicles, wherein said antigen presenting cells have been sensitized to one or more selected antigens, b) a filtration of the culture supernatant of the cells, followed by a tangential ultrafiltration to prepare a sample enriched with membrane vesicles, c) an anion exchange chromatography treatment performed under pressure and a gel permeation chromatography treatment of the sample, and d) a sterilizing filtration step of the sample.

5. Process according to claim 4, wherein the enrichment step also comprises a clarification stage.

6. Process according to claim 4, wherein the enrichment step comprises an affinity chromatography step.

7. Process according to claim 4, characterised in that the enrichment step comprises a centrifugation step realized at a speed below 1000 g or a filtration.

8. Process according to claim 1, wherein the membrane vesicles have a diameter between approximately 60 and 90 nm.

9. Process according to claim 1, wherein the antigen presenting cells comprise dendritic cells, B lymphocytes, macrophages or mastocytes.

10. Process according to claim 4, characterized in that the membrane vesicles are vesicles produced by human dendritic cells.

11. A process of preparing membrane vesicles, characterized in that it comprises the following steps:
   a) obtaining a population of immature dendritic cells sensitized to one or more selected antigens,
   b) culturing the dendritic cells under conditions enabling the production of membrane vesicles,
   c) treating the culture supernatant of said cells to produce a biological sample enriched with membrane vesicles by a filtration of the culture supernatant followed by a tangential ultrafiltration,
   d) purifying the membrane vesicles using a process comprising at least an anion exchange chromatography treatment performed under pressure and a gel permeation chromatography of the sample, and,
   e) a sterilising filtration step of the sample.

12. Process according to claim 11, characterized in that the dendritic cells are obtained from a biological sample from a subject.

13. Process according to claim 11, characterized in that during step b), the dendritic cells are cultured under conditions stimulating membrane vesicle production.

14. Process of preparing membrane vesicles from a biological sample, characterized in that it comprises:
   a) the culture of a population of membrane vesicle producing tumoral cells under conditions enabling the release of vesicles,
   b) a membrane vesicle enrichment step comprising a filtration followed by a tangential ultrafiltration,
   c) an anion exchange chromatography treatment performed under pressure and a gel permeation chromatography treatment of the sample, and
   d) a sterilizing filtration step of the sample.

15. Process according to claim 14, wherein the tumoral cells are human tumoral cells.

* * * * *